United States Patent
Hiruma et al.

(10) Patent No.: US 6,548,745 B2
(45) Date of Patent: Apr. 15, 2003

(54) ITALIAN RYE GRASS AND A METHOD OF INTRODUCING ENDOPHYTIC FUNGI INTO AN ITALIAN RYE GRASS

(75) Inventors: Naoya Hiruma; Satoshi Shinozaki, both of Fujinomiya (JP)

(73) Assignee: Corporate Juridicial Person Japan Grassland Farming & Forage Seed Association, Tokyo (JP)

( * ) Notice: Subject to any disclaimer, the term of this patent is extended or adjusted under 35 U.S.C. 154(b) by 305 days.

(21) Appl. No.: 09/789,722

(22) Filed: Feb. 22, 2001

(65) Prior Publication Data

US 2001/0032343 A1 Oct. 18, 2001

(30) Foreign Application Priority Data

Feb. 22, 2000 (JP) ........................................ 2000-044730

(51) Int. Cl.$^7$ ............................................. A01H 300/00
(52) U.S. Cl. ........................ 800/320; 800/295; 800/298; 800/302; 424/93.5; 435/223; 435/243; 435/254.1; 435/256; 435/256.4; 435/911; 504/284; 47/58.1
(58) Field of Search .................... 424/93.5; 800/320, 800/295, 298, 302; 504/284; 47/58.1; 435/223, 256, 256.4, 256.1, 243, 911

(56) References Cited

U.S. PATENT DOCUMENTS 4,940,834 A * 7/1990 Hurley et al. ............... 800/200
5,880,343 A * 3/1999 Hiruma et al. .............. 800/320

* cited by examiner

Primary Examiner—Leon B. Lankford, Jr.
Assistant Examiner—Kailash C. Srivastava
(74) Attorney, Agent, or Firm—Kanesaka & Takeuchi

(57) ABSTRACT

To provide an Italian rye grass with excellent characteristics, and in particular, excellent insect resistance and disease resistance, an endophyte, which is a filamentous endophytic fungus living together with a wild plant occurring in nature, is isolated and artificially grown, and made to live symbiotically in Italian rye grass by inoculating and infecting the grass with the artificially grown endophyte.

10 Claims, No Drawings

ITALIAN RYE GRASS AND A METHOD OF INTRODUCING ENDOPHYTIC FUNGI INTO AN ITALIAN RYE GRASS

BACKGROUND OF THE INVENTION

1. Field of the Invention

This invention relates to an Italian rye grass into which endophytic fungi are introduced and a method of introducing endophytic fungi into Italian rye grass. Italian rye grass is a member of the genus Lolium of the tribe Poeae, which is in the sub-family of grasses known as Pooideae.

2. Description of the Related Art

Lolium in the genus Poa, which belongs to the sub-family of grasses known as Pooideae, includes Italian rye grass (*Lolium multiflorum*), perennial rye grass (*Lolium perenne*), and dock wheat (*Lolium temuletum*). Italian rye grass is also referred to by the Japanese name of rat wheat. This plant not only grows naturally, but is also widely cultivated artificially as meadow grass and is very useful for livestock.

Italian rye grass has many uses, and as it is used over a large area, it is easily prone to disease and insects. There is a large amount of damage due to Bluegrass webworm, and this can be so serious that whole meadows can disappear overnight in locations where the chemical spraying of insect larvae, which have just hatched, has not reached.

Conventional methods of cultivating and growing grasses include the artificial crossing method, selection method, mutation method, cell fusion method and gene insertion method. Due to recent progress in biotechnology, the cultivation period which previously required 10 years or more, has been reduced to several years. As regards genetic insertion, several techniques exist such as a method using agrobacterium, the electroporation method and the particle gun method, and they are now being applied to a large variety of crops.

However, in the case of grasses, it has been pointed out that this genetic insertion is extremely inefficient. For example, it is difficult to infect grasses using the agrobacterium method, so genetic insertion is very difficult. As regards the electroporation method, a regeneration system has to be developed from the protoplast of the grass, and even if such regeneration is possible, the characteristics of the plant may suffer damage due to growth mutations.

Concerning the particle gun method, since genes are introduced randomly into the plant organism or culture, the plant obtained frequently becomes a chimera.

In the case of Lolium including Italian rye grass, cell culture techniques such as cell fusion or genetic insertion require complex operating procedures and they are not very efficient. Thus, there are very few examples where they have successfully been applied efficiently, and there are very few instances where they have been successfully developed on a practical level.

However, there are some wild plants in nature in which filamentous internal fungi, i.e. endophytes, live together with the plant. They grow well in plant tissue, and particularly well in the gaps between cells, i.e. the intercellular spaces.

These endophytes, or symbiotic filamentous fungi, not only have no adverse effect on the host plant but in fact provide it with useful substances, and contribute to help it withstanding environmental stresses.

Enhancement of plant properties by endophytes is known from the literature, e.g. insect resistance (Siegel et al, 1987, Ann. Rev. Phytopathol. 25: 293-3 15), disease resistance (Gwinn and Gavin, 1992, Plant Disease 76: 911–914), environmental stress (drought, etc.) resistance (Arachevalta et al, 1989, Agron. J. 81: 83–90), and growth enhancement (Latch et al, 1985, N.Z.J. Agric. Res. 28: 165–168). It is particularly well-known that, in perennial rye grass infected with endophytes, these endophytes improve insect resistance due to the repelling substances and alkaloids they produce.

Latch et al in New Zealand are searching for an endophyte known as an endosafe which has a low toxicity to livestock and excellent insect resistance by collecting and studying endophytes in perennial rye grass.

However, many of the plants in which these endophytes live have little utility, so it is necessary to introduce them into useful grasses. In this regard, attempts have already been made to introduce endophytes into perennial rye grass which is an important pasture grass. The techniques used may be broadly distinguished as artificial crossing and artificial inoculation.

In artificial crossing, useful characteristics are introduced by pollen using a plant infected by an endophyte as mer. However, in the conventional method, there were limitations on the species and strains which could be crossed with one another. In artificial inoculation, plants or culture tissues are inoculated with endophytes that have been isolated and cultivated.

The inoculation method is capable of introducing a wider range of types, but due to problems of technique regarding cultivation of endophytes, inoculation conditions and conditions of the plant itself, it is limited to perennial rye grass. To increase the infection rate, a method has been reported where callus is used as the plant tissue which is inoculated. However according to this method, it is necessary to develop a plant regenerating system from the callus, hence the method was still limited to perennial rye grass.

The conventional cell cultivation method involves a troublesome procedure and requires considerable training. Its practical application was moreover difficult since culture mutations caused by transformation or cell fusion had an effect on the characteristics being introduced or on other traits.

In the genetic insertion method, it was not possible to introduce specific characteristics if it was not known which genes had an effect on the characteristics and type of plant.

Characteristics related to complex factors such as environmental stress could not be introduced by techniques such as genetic insertion. Moreover, plants grown by cell culture techniques were often found to exhibit decreased seed fertility. In the case of grasses this led to a decline of yield and was therefore fatal.

In view of this situation, growth techniques or improvement of characteristics using endophytes is a totally new approach to solving the above problems.

When endophytes are introduced into plants by artificial inoculation on the other hand, the technique is limited to perennial rye grass due to problems in searching for endophytes and cultivation systems, and it has never been applied to other useful grasses such as Italian rye grass. In callus inoculation, it is essential to develop a regenerating system of the plant into which the endophyte is to be introduced. Moreover, inoculation conditions had not been developed to increase the rate of infection.

At present, useful natural endophytes have been found only in perennial rye grass, tall fescue and meadow fescue resulting in a major limitation to their introductions. In particular, the host plants of these endophytes are foreign types, and no endophytes derived from domestic plants had yet been found that were adapted to Japanese environmental conditions.

OBJECT AND SUMMARY OF THE INVENTION

It is therefore an object of this invention to provide an Italian rye grass into which an endophyte is artificially introduced, and a method of artificially introducing an endophyte into Italian rye grass not infected with endophyte.

Another object of this invention is to provide an Italian rye grass with excellent characteristics, and in particular, excellent insect resistance and disease resistance.

According to one aspect of this invention, there is provided an Italian rye grass produced by artificially introducing filamentous endophytic fungi into plants not containing filamentous endophytic fungi. Here, Italian rye grass includes plants having the scientific name *Lolium multiflorum*, and also includes hybrids of Italian rye grass.

The endophytic fungi may be one or both of Neotyphodium and Gliocladium. The endophytic fungi may produce an insect-resistant alkaloid. The Italian rye grass may also be used as turf. The endophytic fungi may be any of FERM P-14798, 15029, 15030, 15862, 16319, 16320, 16327, 14797, 16103, 17372, 14799, 14800, 16321, 16322, 16323, 16324, 16325, 16326, 16328, 16329 or 17351 deposited at the Japanese National Institute of Bioscience and Human Technology.

The invention relating to a method of introducing endophytic fungi into an Italian rye grass, is a method comprising:

a step for isolating filamentous endophytic fungi living naturally in a symbiotic relationship with a plant, and artificially growing the fungi, a step for artificially inoculating the grass with the artificially grown endophytic fungi, and a step for infecting the grass with the artificially inoculated endophytic fungi.

The endophytic fungi may be artificially inoculated by inoculating conidiospores of said endophytic fungi. The characteristics of the isolated endophytic fungi may be examined, and selected endophytic fungi may be inoculated. The characteristics may be any of insect resistance, disease resistance, environmental stress resistance or growth enhancement.

The endophytic fungi may be one or both of Neotyphodium and Gliocladium. The said endophytic fungi may produce an insect-resisting alkaloid. The endophytic fungi are any of FERM P-14798, 15029, 15030, 15862, 16319, 16320, 16327, 14797, 16103, 17372, 14799, 14800, 16321, 16322, 16323, 16324, 16325, 16326, 16328, 16329 or 17351 deposited at the Japanese National Institute of Bioscience and Human Technology.

As described above, this invention relates to Italian rye grasses produced by artificially introducing filamentous endophytic fungi, i.e., endophytes, into Italian rye grasses not containing endophytes, and to a method of artificially introducing endophytes into Italian rye grasses.

Therefore, according to this invention, an endophytic fungus, i.e., an endophyte, is introduced into an Italian rye grass, and by making the endophytic fungus live symbiotically in the Italian rye grass, it is possible to confer at least insect resistance and disease resistance. Therefore, the characteristics of the Italian rye grass are improved, and an Italian rye grass having excellent properties can be obtained.

The above and other objects, features and advantages of this invention will be apparent from the following descriptions of practical mode and examples.

The method of introducing endophytes into an Italian rye grass according to another aspect of this invention will now be described in still more detail practically.

Stage 1 Detection of presence or absence of endophyte and isolation of same (1) Detection of endophyte infection An epidermis of leaf with its sheath is removed from a plant collected in a search, the leaf is peeled and stained with aniline blue solution, and any endophyte in the tissue is detected by examination with an optical microscope.

(2) Isolation and culture of endophyte

After sterilizing plant sections confirmed to contain endophyte, the section is transplanted to an endophyte isolation culture and cultured for several months.

(3) Endophyte classification

Isolated endophyte is classified according to the host, or cultured by varying environmental conditions using the flat plate culture method and classified according to its morphology. Alternatively, a liquid culture is performed and the endophyte is classified according to its morphology, or a slide culture is performed and the endophyte is classified according to its morphology.

Stage 2 Alkaloid analysis

Alkaloid produced either by the fungus alone or when living on the plant is analyzed and examined in particular for insect resistance. Analysis for disease resistance, environmental stress resistance and growth enhancement may be made at the same time.

Stage 3 Introduction of endophyte

The isolated endophyte is artificially introduced into the desired or target Italian rye grass. The endophyte may be introduced by directly inoculating the plant with it, alternatively non-differentiated cells such as callus can be inoculated and the plant is regenerated from the callus. An appropriate method should be chosen according to the type of plant in which it is desired to introduce the endophyte.

Stage 4 Confirmation of endophyte presence

An explant from a plant into which endophyte has been introduced is stained with a dye solution, observed with an optical microscope, and the presence of the endophyte or infection by it is detected using the enzyme immunoassay method.

Stage 5 Examination of plants into which endophyte has been introduced (1) Resistance to pests Using plants into which endophyte had been introduced and plants not containing endophyte, larvae of pests are grown, and a survey of pest damage is carried out artificially.

(2) Resistance to disease

Using Italian rye grass into which endophyte has been introduced, and the same Italian rye grass not containing endophyte, resistance to disease is compared by artificially inoculating the two types of plants with pathogenic fungi and examining the extent of disease.

(3) Tests with later generations of plants

Seeds containing endophyte are collected, germinated, and after confirming that the endophyte was present, the aforesaid tests are performed.

DETAILED DESCRIPTION OF THE PREFERRED EMBODIMENTS

EXAMPLE I (1) Detection of endophyte

Endophyte was detected by the following method from various plants in the grass family which are wild grasses and occur naturally.

The epidermis of leaves and leaf sheaths of these plants were removed, and the presence or absence of endophyte in the tissue was confirmed by an optical microscope examination. This confirmation was performed as follows. 5 ml of lactic acid, 10 ml of glycerine, 5 ml of water and several drops of a staining solution of 0.02 g of an aqueous solution of aniline blue were placed on a glass slide. The leaf sheath was peeled away, and the underside epidermis was peeled away toward the leaf vein with forceps. The peeled epidermis was placed on the glass slide, covered with a cover glass, boiled in the flame of a gas burner, and the tissue was observed with an optical microscope. Under these conditions, if endophyte is present, the mycelium appears blue, so the endophyte can be detected by this procedure.

As a result, Neotyphodium endophyte was detected with almost no branching in the intercellular spaces of plants of the genera Poa, Festuca, Agrostis, Milium, Elymus, Glyceria, Bromus, Brylkinia, Brachypodium, Phleum and Digitaria. Gliocladium endophyte was detected with multiple branching in the intercellular spaces of genus Lolium.

(2) Isolation of endophyte

The endophyte in the aforesaid section (1) was isolated by the following method from the various plants in which it was detected.

To isolate the endophyte from the plant, the leaf and leaf sheath were washed with water, immersed in a 70% aqueous solution of ethanol for 10 seconds, immersed in a 2.5% aqueous solution of sodium hypochlorite for 10 minutes, washed three times with sterile water, transferred to an endophyte isolation culture, and cultivated in the dark at 25° C.

The isolation culture was prepared by sterilizing PDA (potato dextrose agar) adjusted to pH 5.6 at 121° C. for 15 minutes, adding 100 mg/l each of penicillin and streptomycin, and pipefting 20 ml portions into each plastic Petri dishes of diameter 9 cm.

After approx. 3–8 weeks, the mycelium was isolated from an explant, and the colonies were removed by a cork borer of diameter 5 mm, transferred to a PDA culture and grown.

(3) Classification and identification of endophytes by using the flat plate culture method The mycelium transplanted to the PDA culture was grown in the dark at 25° C., and the colonies formed were examined. On examination, the colonies on the culture were all white filaments, their growth was relatively slow, and they grew to a radius of only about 3 cm in one month.

Of these, the 21 endophytes which were isolated, were deposited at the National Institute of Bioscience and Human Technology which belongs to the Agency of Industrial Science and Technology. The description and deposition numbers of these endophytes are as shown in Table 1.

TABLE 1

| Host plant family | Host plant genus | Endophyte | Deposition No. (FERM P) |
|---|---|---|---|
| Trib. Poeae | Poa | Neotyphodium | 14798 |
| " | " | " | 15029 |
| " | " | " | 15030 |
| " | " | " | 15862 |
| " | " | " | 16319 |
| " | " | " | 16320 |
| " | " | " | 16327 |
| " | Festuca | " | 14797 |
| " | " | " | 16103 |
| " | " | " | 17372 |
| Trib. Aveneae | Agrostis | " | 14799 |
| " | " | " | 14800 |

TABLE 1-continued

| Host plant family | Host plant genus | Endophyte | Deposition No. (FERM P) |
|---|---|---|---|
| Trib. Poeae | Milium | " | 16321 |
| Trib. Triticeae | Elymus | " | 16322 |
| Trib. Meliceae | Glyceria | " | 16323 |
| Trib. Bromeae | Bromus | " | 16324 |
| Trib. Brylkinieae | Brylkinia | " | 16325 |
| Trib. Triticeae | Brachypodium | " | 16326 |
| Trib. Aveneae | Phleum | " | 16328 |
| Trib. Paniceae | Digitaria | " | 19329 |
| Trib. Poeae | Lolium | Gliocladium | 17351 |

(4) State of mycelium by slide culture

A PDA culture of thickness 2–3 mm was mounted on a glass slide, mycelium was grown on the culture, and the morphology of the mycelium and conidiospores was examined. This culture was performed at 25° C. in the dark.

On examination, it was found that all the mycelia were colorless, partitions of width 1–2 um being observed throughout. All the isolated Neotyphodium endophyte, excepting FERM P-17372, was able to form conidiospores on observation whether conidiospores grows or not. For Gliocladium endophyte, the formation of conidiospores was not observed.

The conidiospores were formed at the ends of single phialides emerging from the ends or sides of the mycelium, and most were single conidiospores.

All conidiospores were colorless, and monocellular. Most conidiospores were kidney-shaped and were 3–8×1–3 um in size. The phialides formed were all cylindrical tapering towards the ends, and separated from the mycelium by partitions.

(5) Analysis of alkaloids from plants

An alkaloid analysis was performed by the following method for all host plants in Table 1 in which endophyte had been detected.

After freeze-drying the leaves and leaf sheaths of these specimens, a 100 mg sample was placed in a mortar and crushed, 1.5 ml each of methanol and chloroform were added and blended, and the liquid was recovered in a centrifuge sedimentation tube. The mixture was carefully blended for 30 minutes at 18° C., 3 ml each of n-hexane and water were added and the mixture was stirred for 30 minutes. After centrifuging at 2000 r.p.m. for 10 minutes, an organic layer and an aqueous layer were pipetted off.

3 ml of the aqueous layer was purified on a Biorad AG2×8 and an Analytichem Bloud Elut CBA column, and after concentration, 100 ul of 80% methanol was added, 20 ul of each sample was dripped onto a thin layer plate used with Merck silica gel 60, and using a chloroform, methanol, acetic acid and water mixture in the ratio 20:10:1:1 as developer, an analysis was performed by TLC (thin layer plate chromatography).

A 500 ul sample of the organic layer fraction was placed in a 2 ml Eppendorf tube, and after completely evaporating off the solvent in a rotary evaporator, the residue was diluted to 200 ul with chloroform. After dilution, 3 ul of each sample was dripped onto a thin layer plate coated with Merck silica gel 60, and an analysis was performed by TLC using chloroform and methanol in the ratio 4:1 as developer with the addition of 100 ppm of Chanoclavinel as a specimen.

After developing, the water layer and organic layer extracts were confirmed by UV. The color reaction and Rf values were measured using the Ehrlich reagent (solution of 1.0 g p-dimethylbenzaldehyde in 96% ethanol) and nitrosonapthol reagent.

In the aqueous layer extract from the host plant, using the Ehrlich reagent, bluish-purple spots were found. This color reaction with reagent and the Rf value confirmed that these were due to the presence of an indole alkaloid.

In the organic layer extract from the host plant, using the Ehrlich reagent, bluish-purple spots were found for all plants. Using nitrosonaphthol reagent, reddish-purple spots were found at the same positions. Spots were also found in the vicinity of Rf 0.1 as with specimen Chanoclavinel. These color reactions with reagent confirmed production of Chanoclavinel and several indole alkaloids.

(6) Liquid culture

After growing mycelia of the endophytes shown in Table 1 for 2 months on a PDA culture at 25° C. in the dark, colonies were removed by a cork borer of diameter 5 mm, 100 ml of PD (potato dextrose) broth was placed in each of 300 ml flasks with shaking, the colonies were introduced in each flask by an apparatus which had been sterilized at 121° C. for 15 minutes, and shaking was performed at 25° C. with a back and forth motion at 150 r.p.m. As a result, all the fungi spread through all the flasks in one month.

(7) Suppression of pathogenic fungi in vitro

A test of antifungal activity was performed using respectively the leaf rot fungus Rhizoctronia sp., leaf withering fungus Drechslera sp. and Dallas spot fungus Sclerotinia sp. which occur in Italian rye grass.

This test was performed by shaking the endophytes in Table 1 in 100 ml of a PD culture, and removing those which had a degree of light absorption in the vicinity of 1.0. After filtering the mycelium, agar was added to the filtrate to solidify it in a Petri dish, 5 mm diameter colonies of each pathogenic fungus were placed in the center, and the cultures grown for 7 days.

The propagation distance of the mycelium from the center was measured. Endophytes which suppressed propagation to less than 2 cm from the center were referred to as A, those which suppressed it to less than 3 cm were referred to as B, and the remainder were referred to as C. Almost all endophytes showed the strong suppressive activity of A or B. Table 2 and Table 3 show the results.

For the endophytes shown in Table 1, an insect resistance test, environmental stress test and growth enhancement test were also performed. These tests were used as a criterion for endophyte selection.

TABLE 2

In vitro activity of Neotyphodium endophytes

| Host plant genus | Endophyte (FERM P.) | Conidiospore formation | Rhizoctonia Suppressive activity | Drochslera Suppressive activity | Sclerotinia Suppressive activity |
|---|---|---|---|---|---|
| Poa | 14798 | + | A | A | B |
| | 15029 | + | B | A | B |
| | 15030 | + | B | B | A |
| | 15862 | + | A | A | A |
| | 16319 | + | B | A | A |
| | 16320 | + | B | B | B |
| | 16327 | + | B | A | A |
| Festuca | 14797 | + | B | B | A |
| | 16103 | + | A | A | B |
| | 17372 | − | A | A | A |
| Agrostis | 14799 | + | B | A | B |
| | 14800 | + | B | A | B |
| Milium | 16321 | + | A | A | A |
| Elymus | 16322 | + | B | B | B |
| Glyceria | 16323 | + | B | B | B |
| Broms | 16324 | + | A | A | A |
| Brylkinia | 16325 | + | B | A | B |
| Brachypodium | 16326 | + | B | A | A |
| Phleum | 16328 | + | B | B | B |
| Digitaria | 16329 | + | C | C | B |

TABLE 3

In vitro activity of Gliocladium endophytes

| Host plant genus | Endophyte (FERM P.) | Conidiospore formation | Rhizoctonia Suppressive activity | Curvularia Suppressive activity | Sclerotinia Suppressive activity |
|---|---|---|---|---|---|
| Lolium | 17351 | — | A | A | B |

(8) Artificial inoculation using plants

Artificial inoculation of Italian rye grass was performed using the isolated endophytes. The plants used here were the Italian rye grasses Waseaoba, Surrey, Horida 80, Grazer, Major, Total, Sultan; the hybrid rye grass Grossland Ariki, and the intermediate rye grasses Tetrelite, Gladiator.

The aforesaid endophytes were first grown according to the method of (2), transferred to a fresh PDA culture, and cultured under the same conditions for 5–12 days. For the inoculation, seeds were sterilized and sown on a WA culture (Water Agar culture) comprising 0.8% agar added to water, and cultivated under dark conditions. 3–7 days after starting the culture, a notch was formed in the growth point of the plant with a knife, and mycelia cultured on the PDA medium were inserted.

After 8 days in the dark at 25° C. and 30° C., the plants were cultivated for 4 hours under illumination at 15° C. for 16 hours, and cultivated under illumination at 25° C. for 16 hours for at least 2 days. Plants which had turned green were acclimatized in pots.

By applying the method described in section (1) to confirm the presence of endophyte, it was found that endophytes had been introduced into the plants. When artificial inoculation was performed using plural endophytes, two endophytes were inoculated by the method of (8) using FERM P-15862 as Neotyphodium endophyte and FERM P-17351 as Gliocladium endophyte.

On observing the tissue using the method of section (1) after inoculation, infection by both of the endophytes Neotyphodium and Gliocladium was confirmed. Further it was also found that the infection rate was higher using the two endophytes than by using each endophyte separately.

(9) Artificial inoculation using callus

Callus was induced in Italian rye grass as a specimen for artificial inoculation. Using the above species, a callus induction culture was prepared by adding 2.0 mg/l of 2,4-D(2,4-dichlorophenoxyacetic acid) and 0.2 mg/l of BAP (6-benzylaminopurine) to an MS base culture.

Seedlings obtained immediately after germination on the MS culture were transplanted to callus induction cultures, and cultured for 2 months in the dark at 25° C. so as to obtain callus which had differentiating ability.

Artificial inoculation was performed using callus from Italian rye grass with all endophytes, i.e., Neotyphodium and Gliocladium. The callus was induced on the aforesaid induction culture, and then transferred to the MS base culture without addition of plant hormone.

Immediately after transferring, the callus was cut with a knife, and 50 ul of mycelium per callus, grown as in section (6), was dripped in.

The callus was cultured for several weeks in the dark at 25° C. and 30° C., then placed under illumination for 16 hours, or alternatively it was placed under illumination for 16 hours from the start. The regenerated plant was then transferred to a fresh MS culture and grown for one month. When an examination was made for presence of endophyte according to the method described in section (1), it was confirmed that endophyte had been introduced.

(10) Mass production of conidiospores

Conidiospores were mass produced for all the Neotyphodium endophytes forming conidiospores of the endophytes shown in Table 1. These fungi were cultured by the same method as that of section (6), and transferred to a fresh PD culture. 20 ml of culture liquid was removed after 5–12 days when the ability to form conidiospores is at a peak, and unwanted mycelium was removed by two superimposed 20 um meshes. 10 ml of the filtrate was placed in a centrifuge tube, and centrifugation was performed at 1000 r.p.m. for 10 minutes. After centrifuging, the supernatant liquid was discarded and 1 ml of PD culture was added so as to obtain a suspension of conidiospores.

(11) Inoculation method using conidiospores

Species of Italian rye grass were artificially inoculated with a conidiospore suspension of the Neotyphodium endophytes shown in Table 1, using the callus inoculation method described in section (9). After examining the plants obtained by the methods described in (1), very many plants were found to contain the endophyte, and there was a significant difference compared to the inoculation method of section (9) using the mycelium.

(12) Detection of endophyte by enzyme immunoassay (ELISA)

The endophyte was detected by the following method from leaves of plants in which endophyte had been introduced by the artificial inoculation of sections (8), (9) and (11).

Buffer solution was added to 0.5 g raw weight of an explant, and the mixture was crushed in a mortar so as to obtain an extract. 50 ul of this extract was placed in a well in a microplate, and adsorbed at room temperature for 30 minutes. Uncombined antigen was washed out.

The well was filled with blocking solution (3% skimmed milk solution) and washed 30 minutes later. Anti-endophyte rabbit antiserum (primary antibody) was added to the well, and reacted at room temperature for 60 minutes. Uncombined antibody was washed out.

Diluted secondary antibody (antirabbit IgG goat labeled with alkali phosphatase) was added to the well, and reacted at room temperature for 60 minutes. Uncombined antibody was washed out. A basic solution was then added to the well so as to cause an alkali phosphatase reaction. The reaction was stopped by 0.5N NaOH, and the degree of light absorption at 405 nm was measured.

As a result, all plants into which endophyte had been introduced in sections (8), (9) and (11) gave a color reaction, thus confirming the introduction of these endophytes into Italian rye grass.

(13) Resistance to webworm

The resistance to webworm was examined using the Waseaoba species of Italian rye grass infected by the method of section (8) above.

For Waseaoba (E+) infected with endophyte, plants in the second month after inoculation were acclimatized and then used. As a comparative group, seeds of Waseaoba (E−) which had not been inoculated, and which had been immersed for 10 seconds in 70% ethanol, washed for 10 minutes in 2.5% aqueous sodium hypochlorite solution, rinsed three times with sterilized water, dried, transferred to an MS culture, and cultivated for 2 months after germination, were acclimatized and then used.

Sections of length approximately 1 cm were cut respectively from leaves of Waseaoba (E+) and Waseaoba (E−), and placed three at a time in a Petri dish of diameter 9 cm. Approximately 200 webworm larvae were introduced immediately after hatching, and the extent of the damage of the leaves was observed after 24 hours. Here, leaves which had been eaten 100% were referred to as A, leaves which had been eaten to the extent of only about 70–80% were referred to as B, and the remainder were referred to as C. As a result, as shown in Table 4 and Table 5, damage was observed in the case of Waseaoba (E−), but Waseaoba (E+) showed strong insect resistance as A or B.

(14) Resistance to pathogenic fungi in plants

The pathogenic fungi Drechslera sp., Rhizoctonia sp., and Sclerotinia sp. isolated from withering leaves in Italian rye grass, were respectively cultured for 2 weeks on a PDA medium. The mycelia in the conidiospores formed on the surface of the colonies were then removed with a needle, suspended in sterilized water and number of mycelia adjusted to a concentration of 5000–10000/ml.

For Waseaoba (E+) infected with endophyte, plants in the second month after inoculation were used. As the comparative group, Waseaoba (E−) which had not been inoculated was immersed for 10 seconds in 70% ethanol, washed for 10 minutes in 2.5% aqueous sodium hypochlorite solution, rinsed three times with sterilized water, dried, transferred to an MS culture, and cultivated for 2 months after germination. These were placed in rows of 10 in 6×6×10 cm plant boxes filled with sterilized culture earth, and cultured for 2 weeks.

In inoculation with pathogenic fungi, the whole surface of the plants was sprayed or coated, and the plants then cultivated for one month under 16 hour daylight conditions at 28° C. For the measurements, plants completely without disease were referred to as A, plants which were about 30 percent diseased were referred to as B, and the remainder were referred to as C.

As a result, for all fungi, in the comparative group which did not contain endophyte, the tips of the leaves began to rot in the first week after inoculation, and the plants were completely dead at 3 weeks, however in Waseaoba (E+) containing endophyte, although there were black spots on the leaves of approximately 2 mm diameter in the initial stage of infection, and about 1 cm of leaf withering was detected at the tips of the leaves, there was almost no subsequent spreading of these spots. This showed a clear significant difference regarding leaf withering due to damage caused by Drechslera sp., Rhizoctonia sp., and Sclerotinia sp. The results of resistance to pathogenic fungi are shown together with resistance to webworm in Table 4 and Table 5.

using 200 lawn cutworms immediately hatching of the larvae, by an identical method to that of section (13).

On examination, it was found that whereas Waseaoba (E−) had been completely ravaged, only a small part of Waseaoba (E+) had been eaten.

Next, identical plants to those of section (13) were placed in 20×30 cm pots, 10 cm×10 cm turfs of Waseaoba (E+) and Waseaoba (E−) were prepared, approximately 50 larvae were respectively introduced two weeks after hatching, and after 4 days, the damage was examined.

On examination, whereas Waseaoba (E−) was completely damaged, Waseaoba (E+) fully retained its green leaves.

Identical turfs were propagated vegetatively. Namely 1 m2 turfs of Waseaoba (E+) and Waseaoba (E−) were prepared outdoors, 7 larvae at three weeks or more after hatching were left on each block, and the damage was examined.

On examination, whereas damage did appear gradually, and Waseaoba (E−) had been completely ravaged after 4 days, Waseaoba (E+) had fully retained its green leaves.

(2) Insect resistance using later generations of endophyte-containing plants

Seeds of Waseaoba (E+) which had been artificially inoculated and Waseaoba (E−) in the comparative group

TABLE 4

Activity of Neotyphodium endophytes in infected Italian Rye Grass

| Endophyte (FERM P.) | Infection rate (%) | Rhizoctonia Suppressive activity | Drechslera Suppressive activity | Sclerotinia Suppressive activity | Webworm resistance |
|---|---|---|---|---|---|
| 14798 | 50 | A | A | A | A |
| 15029 | 50 | A | A | B | A |
| 15030 | 60 | B | A | A | A |
| 15862 | 80 | A | A | A | A |
| 16319 | 50 | B | A | A | A |
| 16320 | 40 | B | B | A | A |
| 16327 | 40 | B | A | A | A |
| 17372 | 80 | A | A | A | A |
| 14797 | 70 | A | B | A | B |
| 16103 | 70 | A | A | B | B |
| 14799 | 50 | B | A | B | A |
| 14800 | 50 | B | A | B | A |
| 16321 | 60 | A | A | A | A |
| 16322 | 70 | B | B | B | A |
| 16323 | 70 | B | B | B | A |
| 16324 | 60 | A | A | A | A |
| 16325 | 40 | B | A | B | A |
| 16326 | 80 | B | A | A | A |
| 16328 | 80 | B | B | B | A |
| 16329 | 30 | C | C | B | B |

TABLE 5

Activity of Gliocladium endophytes in infected Italian Rye Grass

| Endophyte (FERM P.) | Infection rate (%) | Rhizoctonia Suppressive activity | Curvularia Suppressive activity | Sclerotinia Suppressive activity | Webworm resistance |
|---|---|---|---|---|---|
| 17351 | 70 | A | A | A | A |

EXAMPLE 2

(1) Resistance to Japanese lawn cutworm

The resistance to Japanese lawn cutworm was examined using Italian rye grass into which endophyte had been introduced according to section (7) of Example 1. This test was performed by examining for damage after 24 hours were collected after earing, endophyte was detected by the method of section (1) in Example 1 after germination, and an insect resistance test was performed by an identical method of section (13) in Example 1. As a result, it was found that, whereas leaf sections of plants of Waseaoba (E+) after germination had no damage at all, Waseaoba (E−) was completely ravaged. From this, it was confirmed that the result obtained due to the presence of endophyte was identical in the case of propagation to later generations via seeds.

Having described specific embodiments of this invention, it is to be understood that the invention is not limited to those precise embodiments, and that various changes and modifications may be made by one skilled in the art without departing from the scope or spirit of the invention as described in the appended claims.

What is claimed is:

1. An Italian rye grass produced by artificially introducing isolated filamentous endophytic fungi Neotyphodium, Gliocladium or their strains into *Lollium multiflorun* or hybride of an Italian rye grass not containing filamentous endophytic fungi.

2. An Italian rye grass as defined claim 1, wherein said endophytic fungi produce an insect-resistant alkaloid.

3. An Italian rye grass infected with endophytic fungi as defined in claim 1, wherein said Italian rye grass is used as turf.

4. An Italian rye grass as defined in claim 1, wherein said endophytic fungi are FERM P-14798, 15029, 15030, 15862, 16319, 16320, 16327, 14797, 16103, 17372, 14799, 14800, 16321, 16322, 16323, 16324, 16325, 16326, 16328, 16329 or 17351 deposited at the Japanese National Institute of Bioscience and Human Technology.

5. A method of introducing endophytic fungi into an Italian rye grass, comprising:

a step for isolating filamentous endophytic fungi Neotyphodium, Gliocladium or their strains living naturally in a symbiotic relationship with a plant, and artificially growing said fungi, a step for artificially inoculating *Lolium multiflorum* or hybrids of an Italian rye grass with said artificially grown endophytic fungi, and a step for infecting said Italian rye grass with said artificially inoculated endophytic fungi by causing them to live symbiotically.

6. A method of introducing endophytic fungi into an Italian rye grass as defined in claim 5, wherein said endophytic fungi are artificially inoculated by inoculating conidiospores of said endophytic fungi.

7. A method of introducing endophytic fungi into an Italian rye grass as defined in claim 5, wherein the characteristics of said isolated endophytic fungi are examined, and selected endophytic fungi are inoculated.

8. A method of introducing endophytic fungi into an Italian rye grass as defined in claim 7, wherein said characteristics are insect resistance, disease resistance, environmental stress resistance or growth enhancement.

9. A method of introducing endophytic fungi into an Italian rye grass as defined in claim 7, wherein said endophytic fungi produce an insect-resisting alkaloid.

10. A method of introducing endophytic fungi into an Italian rye grass as defined in claim 5, wherein said endophytic fungi are FERM P-14798, 15029, 15030, 15862, 16319, 16320, 16327, 14797, 16103, 17372, 14799, 14800, 16321, 16322, 16323, 16324, 16325, 16326, 16328, 16329 or 17351 deposited at the Japanese National Institute of Bioscience and Human Technology.

* * * * *